United States Patent [19]

Bogdanovic

[11] 4,329,301

[45] May 11, 1982

[54] METHOD OF PREPARING DI-ORGANO-MAGNESIUM COMPOUNDS

[75] Inventor: Borislav Bogdanovic, Mulheim an der Ruhr, Fed. Rep. of Germany

[73] Assignee: Studiengesellschaft Kohle mbH, Mulheim an der Ruhr, Fed. Rep. of Germany

[21] Appl. No.: 123,157

[22] Filed: Feb. 21, 1980

[30] Foreign Application Priority Data

Feb. 20, 1979 [AT] Austria .................................. 1314/79

[51] Int. Cl.$^3$ ............................................... C07F 3/02
[52] U.S. Cl. ................................................ 260/665 R
[58] Field of Search .................................... 260/665 R

[56] References Cited

U.S. PATENT DOCUMENTS

| | | | |
|---|---|---|---|
| 2,959,625 | 11/1960 | Blitzer et al. | 260/665 G |
| 2,985,692 | 5/1961 | Podall | 260/665 G |
| 3,354,190 | 11/1967 | Ramsden | 260/665 G X |
| 3,388,179 | 6/1968 | Ramsden | 260/665 G |
| 3,706,809 | 12/1972 | Moroe et al. | 260/655 R |

OTHER PUBLICATIONS

Chemical Abstracts, 53, 4134g (1959) Abstract of Ital. 548183, Sep. 19, 1956.

*Primary Examiner*—Helen M. S. Sneed
*Attorney, Agent, or Firm*—Sprung, Horn, Kramer & Woods

[57] ABSTRACT

A method of preparing a di-organo-magnesium compound of the formula $R_2Mg$ in which R is an organic radical bonded to Mg by carbon, comprising reacting magnesium hydride $MgH_2$ or magnesium and hydrogen with an olefin in the presence of a catalyst comprising a compound of a transition metal of the 4th to 8th secondary group and an organometallic compound or a hydride of a metal of the 1st to 3rd principal groups of the periodic system. Advantageously there is also present a polycyclic aromatic compound or a tertiary amine as activator and the reaction is effected in the presence of tetrahydrofuran as solvent at a pressure of about 1 to 300 bars at about 0° to 200° C., the atomic ratio of Mg:transition metal being from about $10^4$ to 10:1, the molar ratio of transition metal compound:organometal compound or metal hydride being from about 0.1 to 10:1, the molar ratio of olefin:magnesium being from about 2 to 10:1 and the olefin being of the formula $CH_2=CHR'$ wherein R' is H or an alkyl, cyclo-alkyl, aryl or aralkyl group.

20 Claims, No Drawings

METHOD OF PREPARING DI-ORGANO-MAGNESIUM COMPOUNDS

BACKGROUND

The invention relates to a catalytic method of preparing di-organo-magnesium compounds by the reaction of magnesium hydride, or of magnesium and hydrogen, with olefins.

Di-organo-magnesium compounds are usually prepared from Grignard compounds by disproportioning them with dioxane or other Lewis bases (K. Nutzel in Houben-Weyl, "Methoden der organischen Chemie", Vol. 13/2a, p. 197).

$$2RMgX \rightarrow R_2Mg + MgX_2 \qquad (1)$$

According to U.S. Pat. No. 4,069,267 and the patent literature cited therein, di-organo-magnesium compounds can be prepared by the reaction of magnesium with alkyl halides followed by reaction with lithium alkyls in hydrocarbons. A disadvantage of this last-named method is the need to use expensive lithium alkyls.

Attempts to prepare di-organo-magnesium compounds directly from magnesium, olefin and hydrogen have hitherto achieved little success. According to H. E. Podall and W. E. Foster (J. Org. Chem., 23, 1848 (1958)), an uncatalyzed reaction of magnesium hydride with ethylene and other alpha olefins in various media and under various reaction conditions produces dialkyl magnesium compounds in poor yields. If, for example, a magnesium hydride synthesized from magnesium and hydrogen or by other methods is reacted with ethylene, only 4 to 7% of diethyl magnesium is obtained. The maximum yield of diethyl magnesium, of 28%, is achieved only when so-called "active magnesium hydride" is used, which is prepared from lithium aluminum hydride and diethyl magnesium. Accordingly, this synthesis assumes the use of diethyl magnesium prepared by some other method as the starting material.

An addition of magnesium hydride onto olefins and alkynes in tetrahydrofuran catalyzed with 5 mole-% of bis(cyclopentadienyl)titanium dichloride ($Cp_2TiCl_2$) has been reported recently (E. C. Ashby, T. Smith, J.C.S. Chem. Comm., 30 (1978)). In this case, too, however, an "active magnesium hydride" prepared from diethylmagnesium and $LiAlH_4$ was used. Therefore these methods are not used in the preparation of di-organo-magnesium compounds on a technical scale.

According to U.S. patent application Ser. No. 8,739 filed Feb. 2, 1979, now abandoned, the disclosure of which is incorporated herein by reference, magnesium and hydrogen can be transformed catalytically under mild conditions to magnesium hydride in tetrahydrofuran, for example, by using as catalysts combinations of a compound of a transition metal of the fourth to eighth secondary groups and an organometallic compound or a hydride of a metal of the first to third principal groups of the periodic system. If desired, the hydrogenation is performed in the presence of an activator such as, for example, a polycyclic aromatic compound and/or a tertiary amine.

THE INVENTION

It has now surprisingly been found that the above-named catalysts for the hydrogenation of magnesium to magnesium hydride are additionally effective as catalysts for the addition onto olefins. The present method, in combination with the above-named method of preparing magnesium hydride, therefore permits direct access to di-organo-magnesium compounds from magnesium, hydrogen and olefins. The synthesis is performed generally such that, in the first step, magnesium is hydrogenated in the presence of a catalyst under very mild conditions, e.g., at 20° C., and in the second step magnesium hydride is reacted with an olefin in the presence of the same catalyst, under different conditions, e.g., at elevated temperature. The possibility, however, also exists of reacting magnesium with hydrogen and olefins simultaneously in the presence of the catalysts of the invention to form di-organo-magnesium compounds.

The reaction is performed in a solvent, as a rule. The preferred solvents are tetrahydrofuran or diglyme. But dioxane or ethers are also usable.

Examples of compounds of the transition metals of the fourth to eighth secondary group are halides, alcoholates, enolates, carbonic acid derivatives, pi-allyl compounds and cyclopentadienyl compounds.

Preferred transition metal compounds are chromium and titanium halides for low magnesium alkyls such as $MgEt_2$ or $MgPr_2$ and zirconium of hafnium halides for the magnesium alkyls in which R is greater than $C_3$, an example being $Mg(octyl)_2$, and the preferred organometallic compounds of the metals of the first to third principal groups of the periodic system are organic magnesium compounds such as magnesium anthracene.

Polycyclic aromatic compounds are used as activators, such as, for example, naphthaline, tetracene, pentacene, phenanthrene, perylene, and especially anthracene and/or tertiary amines $NR_3$ in which R represents alkyl, cycloalkyl or aryl groups, such as for example triethylamine or tributylamine or pyridine.

In accordance with the invention, the catalysts can be used in an atomic ratio of Mg to the transition metal of about $10^4$ to 10:1, the molar ratio of the transition metal to the organometallic compound or metal hydride being selectable from about 0.1 to 10:1.

Preferred olefins for the reaction of the invention are alpha-olefins of the type $CH_2=CHR'$ in which R' is hydrogen, alkyl, cycloalkyl, aryl or aralkyl groups, the ratio of olefin to magnesium being selectable from about 2 to 10:1. The reaction is performed at temperatures from about 0° to 200° C., but preferably from about 50° to 150° C., and at pressures of about 1 to 300 bars.

The described method for the first time permits a technical production of highly reactive di-organo-magnesium compounds from magnesium, hydrogen and olefins, obviating the reaction of organic halogen compounds with magnesium (the Grignard method). A new access is also opened to the Grignard compounds, in which, in comparison with the Grignard method, only half of the magnesium comes directly from metallic magnesium, the balance coming from readily available magnesium salts:

$$R_2Mg + MgX_2 \rightarrow 2RMgX \qquad (2)$$

The di-organo-magnesium compounds which can be made by the present method can be used as catalysts for the preparation of highly active Ziegler catalysts for the polymerization of ethylene and stereospecific polymerizations of alpha-olefins and diolefins (Chemical Week, Nov. 29, 1978, p. 40). Furthermore, di-organo-magnesium compounds can be used for those synthetic purposes for which the other organometallic compounds can be used or considered, especially organic lithium and Grignard compounds. In comparison to Grignard compounds, the higher reactivity of di-organo-magnesium compounds is advantageous.

As employed herein, preferred olefins comprise those having 2 to about 12, preferably 2 to about 8 carbon atoms, preferred cycloalkyl moieties thereof being cyclopentyl and cyclohexyl, preferred aryl moieties comprise phenyl and naphthyl, and preferred aralkyl moieties are phenyl- and naphthyl-methyl and -ethyl.

EXAMPLES

All of the experiments in the preparation of organic magnesium compounds are performed in a protective atmosphere (argon, for example).

EXAMPLE 1

Catalytic hydrogenation of magnesium to magnesium hydride (in accordance with U.S. application Ser. No. 8,739):

5.50 g (0.23 mol) of powdered magnesium (50 mesh) is suspended in 100 ml of absolute tetrahydrofuran. 0.05 ml of ethyl bromide is added to the suspension, followed, after half an hour of stirring, by 0.50 g (2.8 mmol) of anthracene. After the sample has been stirred for three hours (to form the magnesium anthracene), 0.48 g (3.0 mmol) of $CrCl_3$ (anhydrous) is added, and stirring is continued for 15 to 20 minutes. The olive green suspension is hydrogenated in an 0.5 liter autoclave equipped with a glass insert and a magnetic stirrer. The initial hydrogen pressure amounts to 90 bars; after 18 hours of stirring of the autoclave contents at 18°–20° C., the pressure falls to 75 bars and remains constant as stirring continues, indicating the complete hydrogenation of the magnesium.

Catalyzed addition of magnesium hydride onto ethylene to form magnesium diethyl:

After the hydrogenation, pressure in the autoclave is relieved down to 1 bar, ethylene is forced in to a pressure of 60 bars, and stirring is performed at 85°–90° C. In order to determine how the addition of magnesium hydride onto ethylene proceeds in relation to time, the catalytic reaction is interrupted in four of the above-described batches after 2.5, 6, 24 and 70 hours, by cooling the autoclave contents to room temperature and letting off ethylene to restore standard pressure. The magnesium diethyl content in the individual batches is determined by filtering the $MgH_2$ out of 5.0 ml of the suspension with a D-4 glass frit filter, hydrolyzing 1.0 ml of the filtrate, and determining the $Mg(OH)_2$ acidimetrically and the ethane volumetrically and by mass spectrometer. After reaction periods of 2.5, 6, 24 and 70 hours at 85° to 90° C., the yield of magnesium diethyl amounts to 44, 71, 83 and 82%, respectively, which signifies that, under the given reaction conditions, the catalytic addition of $MgH_2$ onto ethylene virtually ends after 20 to 24 hours.

EXAMPLE 2

0.05 ml of ethyl bromide is added to a suspension of 5.50 g (0.23 mol) of magnesium powder (50 mesh) in 90 ml of tetrahydrofuran, and, after half an hour of stirring, 0.51 g (2.9 mmol) of anthracene is added. After three hours of stirring, 0.57 g (3.0 mol) of $TiCl_4$, dissolved in 10 ml of THF, is added to the suspension and stirring continues for 15 minutes. The sample is hydrogenated for 22 hours at 20° C. as described in Example 1, the hydrogen pressure in the autoclave diminishing from 88 to 75 bars. Then the pressure is reduced to standard pressure, ethylene is forced in to 60 bars, and the batch is stirred for 22 h at 90° C. The yield of diethyl magnesium, determined as described in Example 1, amounts to 81%.

EXAMPLE 3

0.05 ml of ethyl bromide is added to a suspension of 5.50 g (0.23 mol) of magnesium powder (50 mesh) in 90 ml of THF, and, after half an hour of stirring, 0.80 g (4.5 mmol) of anthracene is added. After 3 h of stirring, 0.87 g (4.6 mmol) of $TiCl_4$, dissolved in 10 ml of THF, is added to the suspension which is then stirred for another 15 to 20 min. The sample is hydrogenated at 20° C. for 26 hours as described in Example 1. During this period the hydrogen pressure diminishes from 90 to 76 bars. The autoclave is relieved to standard pressure, 30 g (0.71 mol) of propene is added to the contents of the autoclave, and the mixture is stirred for 72 h at 85° C. Then the autoclave is cooled down to room temperature and the excess propene is blown off. The now scarcely turbid, black solution is filtered through a D-4 glass frit filter. 1.0 ml of the filtrate (of a total of 82.0 ml) consumes 52.4 ml of 0.1 N hydrochloric acid in the acidimetric titration, corresponding to a yield of $Mg(C_3H_7)_2$ of 95%. The hydrolysis of an aliquot part of the solution yields virtually the calculated amount of propane plus a small amount of propene and hydrogen which have formed by the thermal decomposition of the $Mg(C_3H_7)_2$ by the hydrolysis.

EXAMPLE 4

This experiment was performed similarly to Example 3, using 2.5 times the amount of the catalyst (2.0 g of anthracene and 2.2 g of $TiCl_4$). The yield of $Mg(C_3H_7)_2$ amounts to 98%.

EXAMPLE 5

0.05 ml of ethyl bromide is added to a suspension of 5.50 g (0.23 mol) of magnesium powder (50 mesh) in 100 ml of THF, and after half an hour of stirring, 0.52 g (2.9 mmol) of anthracene is added. After three hours of stirring, 0.47 g (3.0 mmol) of $CrCl_3$ is added and stirring is continued for 15 to 20 minutes. The sample is hydrogenated for 20 hours at 20° C. as described in Example 1, while the hydrogen pressure decreases from 90 to 76 bars. The autoclave is relieved to standard pressure and another portion of the catalyst (composed of 0.50 g Mg, 0.03 ml $C_2H_5Br$, 0.50 g anthracene and 0.46 g $CrCl_3$ as described above), plus 50 g (1.2 mol) of propene, is added. The mixture is then stirred for 70 hours at 120° C. The yield of $Mg(C_3H_7)_2$, determined as described in Example 4, amounts to 25%.

EXAMPLE 6

The experiment was performed similarly to Example 4, using 1-butene (85.0 g = 1.5 mol) instead of propene for the reaction with magnesium hydride. The yield of $Mg(C_4H_9)_2$ after 48 h of reaction at 80° C. amounts to 90–95%.

EXAMPLE 7

The experiment was performed similarly to Example 4, using 84.0 g (0.75 mol) of 1-octene instead of propene for the reaction with magnesium hydride. The yield of $Mg(C_8H_{17})_2$ after 48 h of reaction at ebullition of the mixture (at standard pressure) amounts to 55–60%.

EXAMPLE 8

5.50 g (0.23 mol) of magnesium powder (50 mesh) is suspended in 100 ml of absolute THF. 0.05 ml of ethyl bromide is added to the suspension, followed, after half an hour of stirring, by 0.80 g (4.5 mmol) of anthracene. After three hours of stirring the sample (formation of magnesium anthracene), 0.86 g (4.5 mmol) of $TiCl_4$, suspended in 10 ml of THF, is added, and stirring is continued for 15 to 20 minutes. The dark violet suspension is reacted with hydrogen and ethylene in a half-liter autoclave equipped with a glass insert and a magnetic stirrer. For this purpose, 50 bars of ethylene and 50 bars of hydrogen (total pressure 100 bars) are forced into the autoclave and then the contents of the autoclave are stirred for 24 hours at 85° C. The autoclave is cooled to room temperature and relieved to standard pressure. The batch is filtered and 1.0 ml of the filtrate is hydrolyzed, and the $Mg(OH)_2$ is determined acidimetrically and the ethane volumetrically and by mass spectrometry. The yield of magnesium diethyl amounts to 56% of the theory.

EXAMPLE 9

To prepare the catalyst, 0.5 g (20.6 mol) of magnesium powder (50 mesh) is suspended in 100 ml of THF. The suspension is treated with 0.2 ml of ethyl bromide, and after half an hour of stirring 0.71 g (4.0 mmol) of anthracene is added. After three hours of stirring the batch (formation of the magnesium anthracene), 0.52 g (4.0 mmol) of anhydrous $NiCl_2$ is added, and stirring is continued for 15 to 20 minutes. 5.3 g of the magnesium hydride prepared in accordance with U.S. patent application Ser. No. 8,739 is added to the olive-green catalyst solution, and the mixture is reacted with ethylene in a half-liter autoclave equipped with a glass insert and a magnetic stirrer. For this purpose, ethylene is forced in at 20° C. to a pressure of 60 bars (without stirring), and then the autoclave contents are stirred for 24 h at 90° C. The autoclave is cooled to room temperature and relieved to standard pressure. The suspension is filtered and 1.0 ml of the filtrate is hydrolyzed, and the $Mg(OH)_2$ is determined acidimetrically and the ethane volumetrically and by mass spectrometry. The yield of magnesium diethyl amounts to about 50% of the theory.

EXAMPLE 10

Example 10 is performed similarly to Example 9, with the same amounts of substances, except that $VCl_4$ is used (0.77 g=4.0 mmol) as the catalyst component instead of $NiCl_2$. The yield of magnesium diethyl is 81% of the theory.

EXAMPLE 11

A suspension of 0.5 g (20.6 gram atoms) of magnesium powder (50 mesh) in 5 ml of absolute THF is treated with 0.05 ml of ethyl bromide and, after half an hour of stirring, with 0.80 g (4.5 mmol) of anthracene. After the mixture has been stirred for three hours (formation of the magnesium anthracene), 0.50 ml (4.5 mmol) of $TiCl_4$, suspended in 5 ml of THF, is added, and stirring is continued for 15 to 20 minutes, 90 ml of toluene and 6.20 g of the magnesium hydride prepared according to U.S. patent application Ser. No. 8,739 are added to the dark-violet catalyst solution, and the mixture is reacted with ethylene in a half-liter autoclave equipped with a glass insert and a magnetic stirrer. For this purpose, ethylene is forced in at 20° C. (without stirring) to a pressure of 90 bars, and then the contents of the autoclave are stirred for 24 h at 120° C. The autoclave is cooled to room temperature and relieved to standard pressure. The suspension is filtered, an aliquot part of the filtrate is hydrolyzed, and the $Mg(OH)_2$ is determined acidimetrically and the ethane volumetrically and by mass spectrometry. The yield of magnesium diethyl is 37% of the theory.

EXAMPLE 12

4.35 g (0.18 mol) of magnesium powder (50 mesh) in 100 ml of absolute THF is treated with 0.05 ml of ethyl bromide, and after half an hour of stirring, 0.64 g (3.6 mmol) of anthracene is added. After the mixture has been stirred for three hours 0.58 g (3.7 mmol) of $CrCl_3$ (anhydrous) is added and stirring is continued for 15 minutes. The mixture is then hydrogenated for 20 h at 60 bars of hydrogen pressure in a half-liter autoclave equipped with a glass insert and magnetic stirrer, the magnesium being transformed quantitatively to magnesium hydride. Then, a second catalyst, prepared from 0.50 g (21 mmol) of magnesium powder, 0.03 ml of ethyl bromide, 0.64 g (3.6 mmol) of anthracene and 0.83 g (3.6 mmol) of $ZrCl_4$ (anhydrous) in 10 ml of THF, is added. The preparation of the zirconium catalyst was performed in the same manner as described above in the case of the chromium catalyst. 65 ml of 1-octene (47.0 g, 0.42 mol) is added over a period of 5 h at the refluxing temperature and at standard pressure, and the mixture is stirred for another hour at the boiling temperature. The yield of $Mg(C_8H_{17})_2$ after this period amounts to 72% and, after another 8 h of stirring the mixture at ebulition, it amounts to 90 to 95% of the theory.

EXAMPLE 13

0.50 g (21 mmol) of magnesium powder (50 mesh) in 100 ml of absolute THF is treated with 0.05 ml of ethyl bromide and, after half an hour of stirring, with 0.64 g (3.6 mmol) of anthracene. After three hours of stirring the mixture, 1.28 g (4.0 mmol) of $HfCl_4$ (anhydrous) is added, and stirring is continued for 15 minutes. Now, 5.36 g of the magnesium hydride prepared in accordance with U.S. patent application Ser. No. 8,739 (88%, balance THF) and 65 ml (47.0 g, 0.42 mol) of 1-octene are added and the mixture is heated to the boiling temperature. After 17 h of reaction at the boiling temperature, the yield of $Mg(C_8H_{17})_2$ is 66%, and, after 25 h, 71% of the theory.

It will be appreciated that the instant specification and examples are set forth by way of illustration and not limitation, and that various modifications and changes may be made without departing from the spirit and scope of the present invention.

What is claimed is:

1. A method of preparing a di-organo-magnesium compound of the formula $R_2 Mg$ in which R is an organic radical bonded to Mg by carbon, comprising reacting magnesium hydride $MgH_2$ or magnesium and hydrogen with an olefin in the presence of a catalyst comprising a compound of a transition metal of the 4th to 8th secondary groups and an organometallic compound or a hydride of a metal of the 1st to 3rd principal groups of the periodic system.

2. A method according to claim 1, wherein the reaction is performed in the presence of a solvent.

3. A method according to claim 1, wherein the reaction is effected at a pressure of about 1 to 300 bars.

4. A method according to claim 1, wherein the reaction is effected at from about 0° to 200° C.

5. A method according to claim 1, wherein the atomic ratio of Mg:transition metal is from about $10^4$ to 10:1.

6. A method according to claim 1, wherein the molar ratio of transition metal compound:organometal compound or metal hydride is from about 0.1 to 10:1.

7. A method according to claim 1, wherein the catalyst further comprises a polycyclic aromatic compound or a tertiary amine as activator.

8. A method according to claim 7, wherein the activator comprises a polycyclic aromatic compound selected from the group consisting of naphthalene, anthracene, tetracene, pentacene, phenanthrene and perylene.

9. A method according to claim 7, wherein the activator comprises a pyridine or a tertiary amine of the formula $NR_3$ in which R is an alkyl, cycloalkyl or aryl group.

10. A method according to claim 1, wherein the molar ratio of olefin:magnesium is from about 2 to 10:1.

11. A method according to claim 1, wherein the olefin is of the formula $CH_2=CHR'$ wherein R' is H or an alkyl, cycloalkyl, aryl or aralkyl group.

12. A method according to claim 1, wherein the reactant is magnesium hydride.

13. A method according to claim 1, wherein the reactant is magnesium plus hydrogen.

14. A method according to claim 7, wherein the reaction is effected in the presence of tetrahydrofuran as solvent at a pressure of about 1 to 300 bars at about 0° to 200° C., the atomic ratio of Mg:transition metal being from about $10^4$ to 10:1, the molar ratio of transition metal compound:organometal compound or metal hydride being from about 0.1 to 10:1, the molar ratio of olefin:magnesium being from about 2 to 10:1 and the olefin being of the formula $CH_2=CHR'$ wherein R' is H or an alkyl, cyclo-alkyl, aryl or aralkyl group.

15. The method of claim 1, wherein said transition metal is selected from titanium, zirconium, hafnium, vanadium, chromium and nickel.

16. The method of claim 15 wherein said transition metal is in the form of a halide salt.

17. The method of claim 16 wherein said halide salt is in the form of a chloride.

18. The method of claim 17 wherein said halide salt is zirconium chloride.

19. A method according to claim 1 wherein the catalyst is a compound of a transition metal of the fourth to eighth secondary groups and a hydride of a metal of the first to third principal groups of the periodic system.

20. A method according to claim 1 wherein the catalyst is a compound of a transition metal of the fourth to eighth secondary groups and an organo metallic compound of a metal of the first to third principal groups of the periodic system.

* * * * *